US00PP27679P2

(12) United States Plant Patent
Jones

(10) Patent No.: US PP27,679 P2
(45) Date of Patent: Feb. 14, 2017

(54) ***NEMESIA* PLANT NAMED 'SUNJON 008'**

(50) Latin Name: *Nemesia denticulata×caerulea*
Varietal Denomination: SUNJON 008

(71) Applicant: Jimmy Jones, St. Brides Netherwent (GB)

(72) Inventor: Jimmy Jones, St. Brides Netherwent (GB)

(73) Assignee: Suntory Flowers, Ltd. (JP)

( * ) Notice: Subject to any disclaimer, the term of this patent is extended or adjusted under 35 U.S.C. 154(b) by 0 days.

(21) Appl. No.: 14/756,875

(22) Filed: Oct. 21, 2015

(51) Int. Cl.
*A01H 5/02* (2006.01)

(52) U.S. Cl.
USPC ..... Plt./458

(58) Field of Classification Search
USPC ..... Plt./458
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Nemesia* cultivar named 'SUNJON 008' is disclosed, characterized by cherry pink flowers and terminal bracts, uniform inflorescence and very compact plant form. The new variety is a *Nemesia*, normally produced as an outdoor garden or container plant.

1 Drawing Sheet

Latin name of the genus and species: *Nemesia denticulata×caerulea.*

Variety denomination: 'SUNJON 008'.

BACKGROUND OF THE INVENTION

The new *Nemesia* cultivar is a product of a planned breeding program conducted by the inventor, Jimmy Jones, at a commercial greenhouse in Magor Wales, United Kingdom. The objective of the breeding program was to produce new *Nemesia* varieties for ornamental commercial applications. Selection of this new variety was made during June of 2013.

The seed parent is the unpatented proprietary seedling *Nemesia denticulata* '509'. The pollen parent is the unpatented proprietary variety *Nemesia caerulea* '2523'. The cross pollination resulting in this new variety was made during April 2012.

Asexual reproduction of the new cultivar was performed by vegetative terminal cuttings. This was first performed at a commercial greenhouse in Magor Wales, United Kingdom in October of 2013 and has shown that the unique features of this cultivar are stable and reproduced true to type in multiple successive generations.

SUMMARY OF THE INVENTION

The cultivar 'SUNJON 008' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUNJON 008' These characteristics in combination distinguish 'SUNJON 008' as a new and distinct *Nemesia* cultivar:

1. Unique strong cherry pink coloration to upper flower.
2. Compact plants.
3. Small foliage.

PARENT COMPARISON

Plants of the new cultivar 'SUNJON 008' are comparable to the seed parent variety in most horticultural characteristics; however, the new variety 'SUNJON 008' differs in the following:

1. Upper flower color of the new variety is more pink than red-purple in the new variety.

Plants of the new cultivar 'SUNJON 008' are comparable to the pollen parent variety in most horticultural characteristics; however, the new variety 'SUNJON 008' differs in the following:

1. Foliage of the new variety is smaller and closer together than that of the pollen parent.

COMMERCIAL COMPARISON

Plants of the new cultivar 'SUNJON 008' are comparable to the unpatented commercial variety *Nemesia* 'Mello Rose White'. The two *Nemesia* varieties are similar in most horticultural characteristics; however, the new variety 'SUNJON 008' differs in the following:

1. Corolla size of the new variety is approximately 1.6 cm long and 0.9 cm in height. Corolla size of this comparator is approximately 2.6 cm long, and 2.4 cm in height.
2. Primary flower color of the upper lobe of the new variety is deep Red-purple, near 71A. The same flower part in this comparator is pink to light pink, near Red-Purple N74C to N74D.
3. Secondary flower color of the upper lobe of the new variety is deep Red-Purple, near 71A. The similar flower part in this comparator is colored near Violet 86B, 86C and 86D.
4. Plants of the variety are semi-upright, plants of this comparator are upright and mounding.

BRIEF DESCRIPTION OF THE PHOTOGRAPH

The accompanying photograph in FIG. 1 illustrates in full color a close up of the inflorescences. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SUNJON 008' plants grown from approximately April until mid September, in a greenhouse, in Santa Paula, Calif. The growing temperature ranged from 20° C. to 30° C. during the day and from 15° C. to 25° C. during the night. General light conditions are bright, normal sunlight. Measurements and numerical values represent averages of typical plant types.

Botanical classification: *Nemesia* 'SUNJON 008'.

PROPAGATION

Typical method: Terminal vegetative cuttings.

Time to initiate roots: About 14 days at approximately 18° C.

Root description: Fine, densely fibrous.

Time to produce a rooted cutting: About 21 days at 18° C.

PLANT

Growth habit: Semi-upright annual.

Pot size of plant described: 6 inch.

Height: Approximately 14 cm to top of flowering plane, approximately 13 cm to top of foliage plane.

Plant spread: Approximately 30 cm.

Growth rate: Rapid.

Branching characteristics: Free-branching.

Length of primary lateral branches: Approximately 15 cm.

Diameter of lateral branches: Approximately 0.3 cm.

Quantity of lateral branches: Approximately 4 to 8 branches emerge from a pinch.

Stem:

*Color*.—Near RHS Yellow-Green 144B.

*Texture*.—Glabrous.

Age of plant described: Approximately 20 weeks from 1 rooted cutting.

FOLIAGE

Leaf:

*Arrangement*.—Opposite.

*Quantity*.—Approximately 6 to 10 fully expanded leaves per main branch.

*Average length*.—Approximately 2.8 cm.

*Average width*.—Approximately 1.4 cm.

*Shape of blade*.—Lanceolate.

*Apex*.—Acute.

*Base*.—Truncate.

*Attachment*.—Stalked.

*Margin*.—Shallow serrate.

*Texture of top surface*.—Glabrous.

*Texture of bottom surface*.—Glabrous.

*Color*.—Young foliage upper side: Near RHS Green 137A. Young foliage under side: Near RHS Green 138B. Mature foliage upper side: Near RHS Green 137A. Mature foliage under side: Near RHS Green 138A.

*Venation*.—Type: Pinnate. Venation color upper side: Near RHS Green 137C. Venation color under side: Near RHS Green 138C.

*Petiole*.—Average Length: Approximately 0.4 cm. Diameter: Approximately 0.01 cm. Color: Near Green 137B. Texture: Glabrous.

FLOWER

Natural flowering season: Flowering begins early Spring and continues through Summer.

Inflorescence type and habit: Bilabiate solitary flowers arranged on terminal racemes. Outward and upwardly facing flowers.

Flower longevity on plant: Individual flowers approximately 8 days on the plant without significant color loss or other degradation. Self-cleaning.

Quantity of flowers: Between 15 and 30 racemes per plant, average range 3 to 7 flowers per raceme.

Inflorescence size:

*Diameter*.—Approximately 7.0 cm.

*Height*.—Approximately 8.0 cm.

Peduncle:

*Length*.—Average 5.5 cm.

*Diameter*.—0.15 cm.

*Color*.—Near RHS Green 137C.

*Orientation*.—Straight.

*Strength*.—Strong.

*Texture*.—Glabrous.

Pedicel:

*Length*.—Average 0.8 cm.

*Diameter*.—0.15 cm.

*Color*.—Near RHS Green 137C.

*Orientation*.—Straight.

*Strength*.—Strong.

*Texture*.—Glabrous.

Corolla:

*Length*.—Approximately 1.6 cm.

*Width*.—Approximately 1.5 cm.

*Depth*.—Approximately 0.9 cm.

*Entire corolla length*.—Approximately 3.1 cm.

*Entire corolla width*.—Approximately 0.9 cm.

*Texture*.—Glabrous.

*Aspect*.—75° to 90 ° to stem.

*Persistence*.—Non-persistent.

*Fragrance*.—Very aromatic.

Petals:

*Petal arrangement*.—5 modified petals, 4 upper petals fused at base, forming a lobed upper lip. Single lower petal is larger, functions as nectar guide.

*Upper lip*.—Size: Approximately 0.5 cm in length, approximately 0.4 cm in width. Shape: Elliptic. Apex: Blunt rounded. Margin: Entire. Color: When opening: Upper surface: Near RHS Red-Purple 70A. Lower surface: Near RHS Greyed-Purple N186D. Fully opened: Upper surface: Near RHS Red-Purple 71 A, tinged 70A. Lower surface: Near RHS Red-Purple 72A. Fading: Upper surface: Near RHS Greyed-Purple N187B, when fully faded. Lower surface: Near RHS Greyed-Purple N187B, tinged Greyed-Purple N186D.

*Lower lip*.—Size: Approximately 0.8 cm. in length, approximately 1.5 cm in width. Shape: Reniform. Apex: Obcordate. Margin: Entire, occasional small lobes, slight undulation. Color: When opening: Upper surface: Near RHS White N155A. Lower surface: Near RHS White N155A. Fully opened: Upper surface: Near RHS White N155A. Lower surface: Near RHS White N155A. Fading: Upper surface: Near RHS White N155A. Lower surface: Near RHS White N155A.

Nectar guide: Approximately 0.25 cm, colored near Yellow 4A. Surface glabrous.

Bud:

*Shape*.—Obovate.

*Length*.—Approximately 0.6 cm.

*Diameter*.—Approximately 0.5 cm.

*Color*.—Near RHS Red-Purple 70A, faintly tinged Greyed-Purple N187A.

Calyx: Star shaped, composed of 5 sepals fused at base.

*Sepals*.—Shape: Lanceolate. Apex: Acute. Margin: Entire. Texture: Glabrous. Color: Near RHS 137C, upper and lower surfaces.

REPRODUCTIVE ORGANS

Stamens:

*Number*.—4.

*Filament length*.—Approximately 1 mm.

Anthers:

*Shape*.—Elliptic. Length: Approximately 0.3 mm. Color: Near RHS Yellow 7A. Pollen: Scant. Pollen color: Near RHS Yellow 7A.

Pistil:

*Number*.—1.

*Length*.—Approximately 3.0 mm.

*Style*.—Length: Approximately 0.2 cm. Color: Near RHS Yellow-Green 145A.

*Stigma*.—Shape: Linear. Color: Near RHS Yellow-Green 145A. Ovary color: Near RHS Yellow-Green 145A.

OTHER CHARACTERISTICS

Seeds and fruits: Seed and fruit production has not been observed.

Disease/pest resistance: Neither resistance nor susceptibility observed. *Nemesia* typical diseases include *Pythium* and *Phytopthera*. Various species of White Fly, Aphis and Mites may infect *Nemesia*.

Temperature tolerance: Typically tolerant of temperatures from 5° C. to 35° C.

What is claimed is:

1. A new and distinct cultivar of *Nemesia* plant named 'SUNJON 008' as herein illustrated and described.

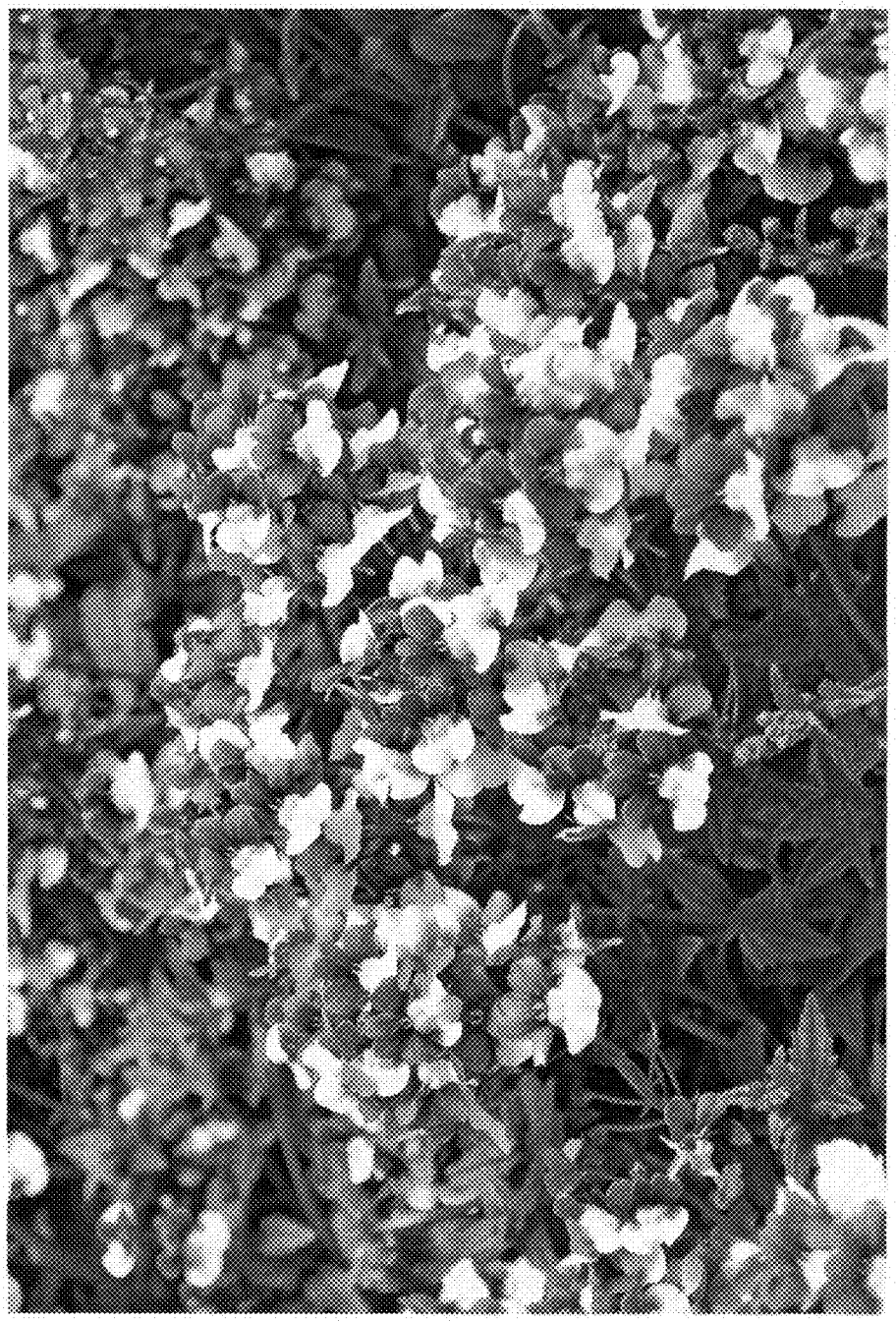

* * * * *